(12) United States Patent
Glover et al.

(10) Patent No.: US 7,297,683 B2
(45) Date of Patent: *Nov. 20, 2007

(54) CRYSTALLINE FORMS OF AN ANTIVIRAL BENZIMIDAZOLE COMPOUND

(75) Inventors: Bobby Neal Glover, Durham, NC (US); Lian-Feng Huang, Durham, NC (US); Robert William Lancaster, Stevenage (GB); Stacey Todd Long, Durham, NC (US); Michele Catherine Rizzolio, Durham, NC (US); Eric Allen Schmitt, Libertyville, IL (US); Barry Riddle Sickles, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 1299 days.

This patent is subject to a terminal disclaimer.

(21) Appl. No.: 10/007,272

(22) Filed: Oct. 29, 2001

(65) Prior Publication Data

US 2002/0177703 A1 Nov. 28, 2002

Related U.S. Application Data

(63) Continuation of application No. 09/647,962, filed as application No. PCT/EP99/02214 on Apr. 1, 1999.

(30) Foreign Application Priority Data

Apr. 7, 1998 (GB) .................................. 9807354.7

(51) Int. Cl.
*A61K 31/70* (2006.01)
*C07H 19/04* (2006.01)

(52) U.S. Cl. ........................................ 514/43; 536/28.9
(58) Field of Classification Search ................ 536/28.9; 514/43
See application file for complete search history.

(56) References Cited

U.S. PATENT DOCUMENTS

| | | | |
|---|---|---|---|
| 3,399,987 A | 9/1968 | Woods et al. | |
| 3,555,040 A | 1/1971 | Frick et al. | |
| 3,655,901 A | 4/1972 | Jensen et al. | |
| 5,248,672 A | 9/1993 | Townsend et al. | |
| 5,360,795 A | 11/1994 | Townsend et al. | |
| 5,473,063 A | 12/1995 | Classon et al. | |
| 5,574,058 A | 11/1996 | Townsend et al. | |
| 5,646,125 A | 7/1997 | Townsend et al. | |
| 5,654,283 A | 8/1997 | Townsend et al. | |
| 5,665,709 A | 9/1997 | Townsend et al. | |
| 5,998,605 A * | 12/1999 | Chamberlain et al. ... | 536/27.11 |
| 6,077,832 A | 6/2000 | Chamberlain et al. | |
| 6,307,043 B1 * | 10/2001 | Chamberlain et al. ..... | 536/28.9 |
| 6,469,160 B1 * | 10/2002 | Glover et al. ............. | 536/28.9 |

FOREIGN PATENT DOCUMENTS

| | | | |
|---|---|---|---|
| WO | WO 9207867 | 5/1992 | |
| WO | WO 9408456 | 4/1994 | |
| WO | WO 9601833 | 1/1996 | |
| WO | WO 9725337 | 7/1997 | |
| WO | WO 9951617 | 10/1999 | |

OTHER PUBLICATIONS

Graul, A., et al., "1263W94 Antiviral", *Drugs of the Future*, vol. 22, No. 7, pp. 707-710 (1997).
Gordon, Irving, et al., "Kinetics of Decay in the Expression of Interferon-Dependent MRNAs Responsible for Resistance to Virus", *Proc. National Academy Sciences USA*, vol. 77, No. 1, pp. 452-456. (Jan. 1980).
Devivar, Rodrigo V., et al., "Benzimidazole Ribonucleosides: Observation of an Unexpected Nitration when Performing Non-Aqueous Diazotizations with t-butyl Nitrite," *Bioorganic & Medicinal Chemistry Letters*, vol. 2, No. 9, pp. 1105-1110.(Sep. 1992).
Tigges, Michael A., et al., "Human CD8+ Herpes Simplex Virus-Specific Cytotoxic T-Lymphocyte Clones Recognize Diverse Viron Protein Antigens", *Journal of Virology*, vol. 66, No. 3, 1622-34. (Mar. 1992).
Devivar, Rodrigo V., et al., "Benzimidazole Ribonucleosides: Design, Synthesis, and Antiviral Activity of Certain 2-(Alkylthio)- and 2-(benzylthio)-5,6-dichloro-1-(B-D-ribofutanosyl) benzimidazoles", *Journal of Medicinal Chemistry*, vol. 37, No. 18, pp. 2942-2949 (Sep. 2, 1994).
Townsend, Leroy B., et al., "Design, Synthesis, and Antiviral Activity Activity of Certain 2,5,6-Trihalo-1-(B-D-ribofuranosyl)benzimidazoles", *Journal of Medical Chemistry*, vol. 38, No. 20, 4098-4105 (Sep. 25, 1995).
Yankulov, Krassimir, et al., The Transcriptional Elongation Inhibor 5,6-Dichloro-1-B-D-ribofuranosylbenzimidazole Inhibits Translation Factor IIH-Associated Protein Kinase, *Journal of Biological Chemistry*, vol. 270, No. 41, pp. 23922-23925.(Oct. 13, 1995).
Nassiri, M. Reza, et al., "Comparison of Benzimidazole Nucleosides and Ganciclovir on the In Vitro Proliferation and Colony Formation of Human Bone Marrow Progenitor Cells," *British Journal of Haematology*, vol. 93, No. 2, pp. 273-279. (May 1996).
Gudmundsson, Kristjan S., et al., "Synthesis and Antiviral Activity of Certain 5'-Modified Analogs of 2,5,6-Trichloro-1-(B-D-ribofuranosyl) benzimidazole," *Journal of Medicinal Chemistry*, vol. 40, No. 5, pp. 785-793 (Feb. 28, 1997).
Fessenden, Ralph J., et al., "Crystallization", *Organic Laboratory Techniques*, 3rd edition, Brooks/Cole (Canada), (2001), only preface and pp. 23-38.
Fieser, Louis D., et al., "Crystallization", *Organic Experiments*, DC Heath and Company, Boston, MA, (1964), only preface and pp. 41-51.
Zou, Ruiming, et al., "Design, Synthesis, and Antiviral Evaluation of 2-Chloro-5-6,dihalo-1-(B-D-ribofuranosyl) benzimidazoles as Potential Agents for Human Cytomegalovirus Infections", *Journal of Medicinal Chemistry*, vol. 40, No. 5, (1997), pp. 811-818. (Feb. 28, 1997).

* cited by examiner

*Primary Examiner*—Shaojia Anna Jiang
(74) *Attorney, Agent, or Firm*—Lorie Ann Morgan (57) ABSTRACT

The invention relates to Form physical forms of 5,6-dichloro-2-(isopropylamino)-1-β-L-ribofuranosyl-1H-benzimidazole, pharmaceutical compositions comprising the same, and their use in medical therapy.

8 Claims, 6 Drawing Sheets

CRYSTALLINE FORMS OF AN ANTIVIRAL BENZIMIDAZOLE COMPOUND

CROSS-REFERENCES TO RELATED APPLICATIONS

This application is a continuation of U.S. patent application Ser. No. 09/647,962, filed 6 Oct. 2000, which is a Rule 371 Application of PCT/EP99/02214, filed 1 Apr. 1999, which claims priority to Great Britain Patent Application No. 9807354.7, filed 7 Apr. 1998.

BACKGROUND OF THE INVENTION

The present invention relates to anhydrous crystalline forms and solvates of the antiviral compound 5,6-dichloro-2-(isopropylamino)-1-(β-L-ribofuranosyl)-1H-benzimidazole (also known as 1263W94; a compound of formula (I)), pharmaceutical formulations comprising anhydrous crystalline forms and solvates of this compound, and their use in therapy.

5,6-Dichloro-2-(isopropylamino)-1-(β-L-ribofuranosyl)-1H-benzimidazole (1263W94) is a benzimidazole derivative useful in medical therapy. WO96/01833 discloses 5,6-dichloro-2-(isopropylamino)-1-(β-L-ribofuranosyl)-1H-benzimidazole and its use for the treatment or prophylaxis of viral infections such as those caused by herpes viruses. The compound as disclosed in WO96/01833 is an amorphous, non-crystalline, hygroscopic material.

The structure of 5,6-dichloro-2-(isopropylamino)-1-(β-L-ribofuranosyl)-1H-benzimidazole, a compound of formula (I) is shown below:

(I)

We have now found that the compound of formula (I) may be prepared in novel crystalline forms and solvates. The novel crystalline forms and solvates of the present invention are more thermodynamically stable than the amorphous form disclosed in WO96/01833. The novel crystalline forms and solvates have the further advantage that they are essentially non-hygroscopic. These crystalline forms and solvates have good storage properties and can be readily formulated into pharmaceutical compositions such as tablets, capsules, and liquid systems. The crystalline forms and solvates may be characterized by their X-ray powder diffraction patterns.

DETAILED DESCRIPTION OF THE INVENTION

According to a first aspect of the invention there is provided the compound of formula (I) in a novel crystalline form, Form I. Form I is defined by the X-ray powder diffraction pattern illustrated in FIG. 1, which is obtained by a properly aligned diffractometer equipped with a diffracted beam curved graphite monochromator using copper Kα X-radiation. Form I may be prepared from a mixture of the amorphous compound of formula (I) and the novel crystalline Form II thereof by suspending and heating in water or toluene at temperatures in excess of 50° C. On heating, the suspension turns to a sticky gum which on continued heating converts to a solid.

In another aspect of the invention there is provided the compound of formula (I) in a novel crystalline form, Form II. Form II is defined by the X-ray powder diffraction pattern illustrated in FIG. 2, which is obtained by a properly aligned diffractometer equipped with a diffracted beam curved graphite monochromator using copper Kα X-radiation. Form II may be produced by crystallization or recrystallization of the amorphous compound of formula (I) from mixtures of methanol and water or methanol and toluene. The initial product of the recrystallization is a methanol solvate which on drying loses methanol to produce Form II.

In a further aspect of the invention there is provided the compound of formula (I) as a solid white free flowing powder (hereinafter referred to as the "ethanolate" or ethanol solvate of the compound of formula (I)). The ethanolate is defined by the X-ray powder diffraction pattern illustrated in FIG. 3, which is obtained by a properly aligned diffractometer equipped with a diffracted beam curved graphite monochromator using copper Kα X-radiation. The ethanolate may be prepared from solutions of the compound in mixtures of ethanol and water or ethanol and toluene mixtures.

In yet a further aspect of the invention, there is provided the compound of formula (I) in a novel crystalline form, Form IV. Form IV is defined by the X-ray powder diffraction pattern illustrated in FIG. 4, which is obtained by a properly aligned diffractometer equipped with a diffracted beam curved graphite monochromator using copper Kα X-radiation. Form IV may be obtained by suspending and heating the amorphous compound of formula (I) in water or toluene at temperatures in excess of 50° C. Form IV may also be obtained by suspending Form II in water for several months.

In a further aspect of the invention, there is provided the compound of formula (I) in a novel crystalline form, Form V. Form V is defined by the X-ray powder diffraction pattern illustrated in FIG. 5, which is obtained by a properly aligned diffractometer equipped with a diffracted beam curved graphite monochromator using copper Kα X-radiation. Form V may be produced by adding water gradually to amorphous compound of formula (I) at around 70° C. with rapid stirring over 2 h. After heating at 65-70° C. with stirring for an additional 7 h, the heating and stirring may be discontinued. The mixture may be allowed to stand at ambient temperature for 2.5 days. The mixture may then be filtered. The resultant grainy white solid residue may be allowed to air dry overnight. Form V may also be prepared by hot water slurry of a mixture of Form II and Form I at 90° C. for 20 minutes. Form V may also be prepared by solubilizing another crystalline form or solvate of the compound of formula (I), preferably Form VI or the ethanolate, in acetonitrile and allowing the solution to stand at ambient temperature until Form V precipitates out of solution.

In a further aspect of the invention, there is provided the compound of formula (I) as a mixture of any two or more of the anhydrous crystalline forms and/or solvates of the present invention, or as a mixture of amorphous material and one or more of the anhydrous crystalline forms and/or solvates of the present invention. The compound of formula (I) may also be isolated by acid/base precipitation.

As used herein, the term "solvate" is a complex of variable stoichiometry formed by a solute (a compound of formula (I)) and a solvent. Solvents, by way of example, include water, methanol, ethanol, or acetic acid. Hereinafter, reference to a compound of formula (I) is to the amorphous form of that compound, unless another form or solvate thereof is specified.

The X-ray powder diffraction pattern of the various anhydrous crystalline forms and solvates of the present invention is determined using conventional techniques and equipment known to those skilled in the art of physical characterization. The diffraction patterns of FIGS. 1-6 were obtained with a Philips X-Pert MPD diffractometer system equipped with a diffracted beam curved graphite monochromator using copper Kα X-radiation and an automatic divergent slit. A xenon proportional counter was used as the detector. The powder sample used to generate the X-ray powder diffraction data was prepared by conventional back filled sample preparation techniques using a 16 mm diameter holder about 2 mm thick.

A powder sample of each of Forms I, II, IV, V, VI and the ethanolate were used to produce the X-ray powder diffraction patterns of FIGS. 1, 2, 4, 5, 6 and 3, respectively. The X-ray diffraction patterns for each of the various forms and solvates are unique to the particular form. Each crystalline anhydrous form or solvate exhibits a diffraction pattern with a unique set of diffraction peaks which can be expressed in 2 theta angles (°), d-spacings (Å) and/or relative peak intensities.

2 Theta diffraction angles and corresponding d-spacing values account for positions of various peaks in the X-ray powder diffraction pattern. D-spacing values are calculated with observed 2 theta angles and copper Kα1 wavelength using the Bragg equation. Slight variations in observed 2 theta angles and d-spacings are expected based on the specific diffractometer employed and the analyst's sample preparation technique. More variation is expected for the relative peak intensities. Identification of the exact crystal form of a compound should be based primarily on observed 2 theta angles or d-spacings with lesser importance placed on relative peak intensities. In a mixture of crystal forms, the strongest diffraction peak for each form may overlap with the diffraction peak of another form. In a mixture of crystal forms, identification may be based on the presence of a lesser intensity peak that does not overlap with the other crystal forms. To identify 5,6-dichloro-2-(isopropylamino)-1-(β-L-ribofuranosyl)-1H-benzimidazole Form I, the single most characteristic 2 theta angle peak occurs at 2.57 degrees, or 34.35 Å d-spacing. To identify 5,6-dichloro-2-(isopropylamino)-1-(β-L-ribofuranosyl)-1H-benzimidazole ethanolate, the single most characteristic 2 theta angle peak occurs at 6.63 degrees, or 13.33 Å d-spacing. To identify 5,6-dichloro-2-(isopropylamino)-1-(β-L-ribofuranosyl)-1H-benzimidazole Form IV, the single most characteristic 2 theta angle peak occurs at 11.78 degrees, or 7.51 Å d-spacing.

It may be desirable to rely upon multiple 2 theta angles or multiple d-spacings for the identification of each of the various anhydrous crystalline forms and/or solvates of the present invention. Each of the various anhydrous crystalline forms and/or solvates of 5,6-Dichloro-2-(isopropylamino)-1-(β-L-ribofuranosyl)-1H-benzimidazole can also be identified by the presence of multiple characteristic 2 theta angle peaks including two, three, four, five, six, seven, eight, nine, or ten of the 2 theta angles which are reasonably characteristic of the particular crystalline form. Typically, Form I can be identified by the presence of X-ray diffraction peaks occurring at at least five of the following positions, expressed in 2 theta angles: 7.90, 10.39, 14.63, 15.79, 20.75, 21.99, 22.77, 24.14, 24.71, and 25.97 degrees. Typically, Form II can be identified by the presence of X-ray diffraction peaks occurring at at least five of the following positions, expressed in 2 theta angles: 7.91, 17.33, 18.23, 19.60, 21.88, 23.24, 23.92, 25.27, 27.70, and 29.21 degrees. The ethanolate can be identified by the presence of X-ray diffraction peaks occurring at at least five of the following positions, expressed in 2 theta angles: 9.07, 10.38, 15.95, 17.72. 20.75, 21.37, 22.96, 23.93, 25.40, and 29.05 degrees. Form IV can be identified by the presence of X-ray diffraction peaks occurring at at least five of the following positions, expressed in 2 theta angles: 9.29, 16.04, 18.67. 22.06, 22.68, 23.34, 24.40, 29.64, 30.92, and 31.62 degrees. Form V can be identified by the presence of X-ray diffraction peaks occurring at at least five of the following positions, expressed in 2 theta angles: 13.30, 18.13, 18.78, 20.41, 21.75, 23.02, 26.87, 28.34, 28.55, and 30.22 degrees.

Some margin of error is present in each of the 2 theta angle assignments and d-spacings reported above. The error in determining d-spacings decreases with increasing diffraction scan angle or decreasing d-spacing. The margin of error in the foregoing 2 theta angles for Forms I, IV, V, and the ethanolate is approximately ±0.05 degrees for each of the foregoing peak assignments. The margin of error in the 2 theta angles for Form II is approximately ±0.09 for each of the foregoing peak assignments. The margin of error in d-spacing values for Forms I, IV, V, and the ethanolate is approximately ±0.05 Angstroms. The margin of error in d-spacing values for Form II is approximately ±0.09 Angstroms.

Since some margin of error is possible in the assignment of 2 theta angles and d-spacings, the preferred method of comparing X-ray powder diffraction patterns in order to identify a particular crystalline form is to overlay the X-ray powder diffraction pattern of the unknown form over the X-ray powder diffraction pattern of a known form. For example, one skilled in the art can overlay an X-ray powder diffraction pattern of an unidentified crystalline form of 5,6-dichloro-2-(isopropylamino)-1-(β-L-ribofuranosyl)-1H-benzimidazole, obtained using the methods described herein, over FIG. 1 and readily determine whether the X-ray diffraction pattern of the unidentified form is substantially the same as the X-ray powder diffraction pattern of Form I. If the X-ray powder diffraction pattern is substantially the same as FIG. 1, the previously unknown crystalline form can be readily and accurately identified as Form I. The same technique can be used to determine if the unidentified crystalline form is any of Forms II, IV, V, or the ethanolate by overlaying the X-ray powder diffraction pattern over FIG. 2, 4, 5, or 3, respectively.

Although 2 theta angles or d-spacings are the primary method of identifying a particular crystalline form, it may be desirable to also compare relative peak intensities. As noted above, relative peak intensities may vary depending upon the specific diffractometer employed and the analyst's sample preparation technique. The peak intensities are reported as intensities relative to the peak intensity of the strongest peak. The intensity units on the X-ray diffraction plot are counts/sec. The absolute counts=counts/time×count time=counts/sec×10 sec. Considering 2 theta angles, d-spacing (Å) and relative peak intensity (I) of the fifteen most intense peaks, obtained by the method of Example 18 below, Form I 5,6-dichloro-2-(isopropylamino)-1-(β-L-ribofuranosyl)-1H-benzimidazole exhibits the following X-ray diffraction pattern characteristics:

| Form I | | |
|---|---|---|
| 2 theta angle (°)[1] | Å[1] | I |
| 7.90 | 11.19 | 58.8 |
| 10.39 | 8.51 | 49.7 |
| 14.63 | 6.05 | 33.3 |
| 15.79 | 5.61 | 46.1 |
| 16.95 | 5.23 | 16.4 |
| 19.24 | 4.61 | 14.4 |
| 20.75 | 4.28 | 29.4 |
| 21.99 | 4.04 | 21.0 |
| 22.77 | 3.90 | 100.0 |
| 24.14 | 3.68 | 35.2 |
| 24.71 | 3.60 | 20.5 |
| 25.72 | 3.46 | 13.9 |
| 25.97 | 3.43 | 43.2 |
| 29.44 | 3.03 | 13.9 |
| 31.09 | 2.87 | 14.7 |

[1]Margin of error = approx. ±0.05

Form II 5,6-dichloro-2-(isopropylamino)-1-(β-L-ribofuranosyl)-1H-benzimidazole is further characterized by the following 2 theta angles, d-spacings, and relative peak intensities of the fifteen most intense peaks, obtained by the method of Example 18 below.

| Form II | | |
|---|---|---|
| 2 theta angle (°)[1] | Å[1] | I |
| 7.91 | 11.17 | 100.0 |
| 10.86 | 8.14 | 10.1 |
| 12.69 | 6.97 | 5.2 |
| 13.65 | 6.48 | 4.7 |
| 14.94 | 5.93 | 8.4 |
| 16.11 | 5.50 | 12.8 |
| 17.33 | 5.11 | 17.5 |
| 18.23 | 4.86 | 18.2 |
| 19.60 | 4.53 | 19.6 |
| 21.88 | 4.06 | 18.8 |
| 23.24 | 3.82 | 19.0 |
| 23.92 | 3.72 | 26.7 |
| 25.27 | 3.52 | 24.5 |
| 27.70 | 3.22 | 34.9 |
| 29.21 | 3.06 | 14.2 |

[1]Margin of error = approx. ±0.09

Form II may also exhibit peaks at essentially the following 2 theta angles: 7.9, 10.9, 16.1, 17.3, 18.2, 19.6, 21.9, 23.9 degrees.

The ethanolate of 5,6-dichloro-2-(isopropylamino)-1-(β-L-ribofuranosyl)-1H-benzimidazole is further characterized by the following 2 theta angles, d-spacings, and relative peak intensities of the fifteen most intense peaks, obtained by the method of Example 18 below.

| Ethanolate | | |
|---|---|---|
| 2 theta angle (°)[1] | Å[1] | I |
| 9.07 | 9.74 | 45.2 |
| 10.38 | 8.52 | 22.7 |
| 15.95 | 5.55 | 40.4 |
| 17.72 | 5.00 | 100.0 |
| 18.96 | 4.68 | 17.2 |
| 19.79 | 4.48 | 18.4 |
| 20.75 | 4.28 | 30.4 |
| 21.37 | 4.16 | 27.7 |
| 21.89 | 4.06 | 19.0 |
| 22.08 | 4.02 | 17.5 |
| 22.96 | 3.87 | 40.6 |
| 23.93 | 3.72 | 41.3 |
| 25.40 | 3.50 | 26.7 |
| 27.65 | 3.22 | 19.8 |
| 29.05 | 3.07 | 25.4 |

[1]Margin of error = approx. ±0.05

The ethanolate may also exhibit peaks at essentially the following 2 theta angles: 6.6, 9.1, 9.4, 10.4, 11.0, 14.7, 16.0, 17.2, 17.7, 18.3, 20.8, 21.4, 23.0, 23.9, 25.4, 27.7, 29.1 degrees.

Form IV 5,6-dichloro-2-(isopropylamino)-1-(β-L-ribofuranosyl)-1H-benzimidazole is further characterized by the following 2 theta angles, d-spacings, and relative peak intensities of the fifteen most intense peaks, obtained by the method of Example 18 below.

| Form IV | | |
|---|---|---|
| 2 theta angle (°)[1] | Å[1] | I |
| 9.29 | 9.51 | 15.6 |
| 11.78 | 7.51 | 12.5 |
| 16.04 | 5.52 | 20.1 |
| 18.67 | 4.75 | 25.1 |
| 19.54 | 4.54 | 11.5 |
| 22.06 | 4.03 | 100.0 |
| 22.39 | 3.97 | 11.6 |
| 22.68 | 3.92 | 17.9 |
| 23.34 | 3.81 | 15.5 |
| 23.68 | 3.75 | 10.0 |
| 24.40 | 3.65 | 28.7 |
| 28.72 | 3.11 | 11.1 |
| 29.64 | 3.01 | 13.0 |
| 30.92 | 2.89 | 26.5 |
| 31.62 | 2.83 | 13.9 |

[1]Margin of error = approx. ±0.05

Form IV may also exhibit peaks at essentially the following 2 theta angles: 7.5, 9.3, 11.8, 16.0, 18.7, 19.4, 19.5, 22.1, 22.7, 24.4, 29.6, 30.9 degrees.

Form V 5,6-dichloro-2-(isopropylamino)-1-(β-L-ribofuranosyl)-1H-benzimidazole is further characterized by the following 2 theta angles, d-spacings, and relative peak intensities of the fifteen most intense peaks, obtained by the method of Example 18 below.

| Form V | | |
|---|---|---|
| 2 theta angle (°)[1] | Å[1] | I |
| 9.07 | 9.75 | 19.1 |
| 9.35 | 9.46 | 14.3 |
| 10.74 | 8.23 | 14.0 |
| 13.30 | 6.65 | 26.1 |
| 17.04 | 5.20 | 18.5 |
| 18.13 | 4.89 | 39.2 |
| 18.78 | 4.72 | 57.0 |
| 20.41 | 4.35 | 39.5 |
| 21.75 | 4.08 | 100.0 |
| 22.71 | 3.91 | 15.8 |
| 23.02 | 3.86 | 20.3 |
| 26.87 | 3.32 | 23.4 |
| 28.34 | 3.15 | 24.7 |
| 28.55 | 3.12 | 51.1 |
| 30.22 | 2.95 | 39.0 |

[1]Margin of error = approx. ±0.05

Form V may also exhibit peaks at essentially the following 2 theta angles: 9.1, 9.3, 10.7, 13.3. 17.0, 18.1, 18.8, 20.4, 21.8, 26.9, 28.6, 30.2 degrees.

Based upon the foregoing characteristic features of the X-ray powder diffraction patterns of Forms I, II, IV, V, and the ethanolate and the methods described herein for obtaining these X-ray powder diffraction patterns, one skilled in the art can readily identify each of these anhydrous crystalline forms or solvates of 5,6-dichloro-2-(isopropylamino)-1-(β-L-ribofuranosyl)-11H-benzimidazole. It will be appreciated by those skilled in the art that the X-ray powder diffraction pattern of a sample of any particular anhydrous crystalline form or solvate, obtained using the methods described herein, may exhibit additional peaks. The foregoing tables provide the fifteen most intense peaks which are characteristic of that particular crystalline form or solvate.

The tables should not be interpreted as an exhaustive list of peaks exhibited by the particular form or solvate.

Other methods of physical characterization can also be employed to identify the anhydrous crystalline forms or solvates of the present invention. For example, melting point, differential scanning calorimetry, infra red spectra, and moisture sorption are all techniques known to those skilled in the art to be useful for the physical characterization of a crystalline form or solvate. These techniques may be employed alone or in combination to characterize a given anhydrous crystalline form or solvate.

The invention relates to the anhydrous crystalline forms and solvates both in pure form and in admixture with other forms or solvates of the compound of formula (I). For example, Form I may be in admixture with any one or more of Forms II, IV, V, or the ethanolate. Alternatively Form I may be in admixture with amorphous compound of formula (I). In another embodiment, Form I is in admixture with both amorphous compound of formula (I) and one or more other crystalline forms or solvates including Forms II, IV, V and the ethanolate. Similarly, any of Forms II, IV, V, or the ethanolate may form admixtures with another form or solvate and/or the amorphous material. One embodiment of the present invention is an admixture of Forms I and V. Another embodiment of the present invention is an admixture of Form II and the amorphous material. Another embodiment of the present invention is an admixture of Forms I, IV, and V. Still another embodiment of the present invention is an admixture of Forms I, IV, V, and the amorphous material. Other admixtures of two or more of the anhydrous crystalline forms or solvates which are contemplated by the present invention can be readily determined by those skilled in the art.

The present invention expressly contemplates the foregoing mixtures of any anhydrous crystalline form or solvate with one or more of the amorphous compound of formula (I), and/or other anhydrous crystalline forms and solvates It should be understood that admixtures of a particular form or solvate with amorphous compound of formula (I) and/or other crystalline forms or solvates may result in the masking or absence of one or more of the foregoing X-ray powder diffraction peaks described above for that particular form. Methods are known in the art for analyzing such admixtures of crystalline forms in order to provide for the accurate identification of the presence or absence of particular crystalline forms in the admixture.

In addition to the foregoing, any of the anhydrous crystalline forms or solvates of the present invention may be in admixture with hydrated crystalline forms. For example in any batch containing the anhydrous crystalline compound of formula (I), there may also be hydrated crystalline forms of the compound.

According to a further aspect, the present invention provides a process for the production of the compound of formula (I) in anhydrous crystalline form which comprises treating the amorphous compound of formula (I) with a solubilising solvent serving to convert an amount of the compound of formula (I) into one or more of the anhydrous crystalline forms and/or solvates.

The invention also provides a process for the production of the compound of formula (I) in an anhydrous crystalline form, said process comprising the steps of:

a) forming or providing compound of formula (I) in solution in free base or salt form;

b) isolating the compound of formula (I) from the solution and optionally removing unbound (damp, non-solvated) solvent leaving the compound of formula (I) in substantially dry form;

c) treating the compound of formula (I) with a solubilizing solvent serving to convert an amount of the optionally dried compound of formula (I) from step b) into the anhydrous crystalline form; and d) isolating the anhydrous crystalline form.

The compound of formula (I) may be prepared by any method known in the art, but preferably by the methods described in WO 96/01833, incorporated herein by reference in its entirety.

The synthesis of the compound of formula (I) generally leads to the formation of the compound in solution in the reaction mixture from which it may be separated and purified as a solid product. The compound of formula (I) may then optionally be dried. A number of factors influence the crystalline form of the solid product and in accordance with the present invention the conditions of separation and/or subsequent processing are adjusted to produce the compound of formula (I) as one particular anhydrous crystalline form or solvate, or as a mixture of two or more anhydrous crystalline forms or solvates.

A suitable solubilizing solvent is preferably a water-soluble organic solvent and should be sufficiently solubilizing and be employed in an amount to allow partial solubilization to effect the conversion and precipitation for example from hydrated crystalline form to the desired anhydrous crystalline form of the compound of formula (I). Advantageously the solvent is eventually removed by drying under vacuum.

The damp compound of formula (I) following the first isolation (as in step b above) is preferably dried, for example at about 30° to about 70° C. to provide substantially dry compound of formula (I).

The present invention also provides crystalline forms and solvates of the compound of formula (I) for use in medical therapy, e.g. in the treatment or prophylaxis, including suppression of recurrence of symptoms, of a viral disease in an animal, e.g. a mammal such as a human. The compound of formula (I) anhydrous crystalline forms and solvates are especially useful for the treatment or prophylaxis of viral diseases such as herpes virus infections, for example, CMV infections, as well as disease caused by hepatitis B and hepatitis C viruses. In addition to its use in human medical therapy, the compound of formula (I) anhydrous crystalline forms and solvates can be administered to other animals for treatment or prophylaxis of viral diseases, e.g. to other mammals.

The present invention also provides a method for the treatment or prophylaxis of a viral infection, particularly a herpes infection, CMV infections, as well as disease caused by hepatitis B and hepatitis C viruses in an animal, e.g. a mammal such as a human, which comprises administering to the animal an effective antiviral amount of the compound of formula (I) as an anhydrous crystalline form or solvate.

The present invention also provides the use of the compound of formula (I) anhydrous crystalline forms and solvates in the preparation of a medicament for the treatment or prophylaxis of a viral infection.

As used herein, the term prophylaxis includes the prevention of infection, the prevention of occurrence of symptoms and the prevention of recurrence of symptoms.

The compound of formula (I) anhydrous crystalline forms and solvates may be administered by any route appropriate to the condition to be treated, but the preferred route of administration is oral. It will be appreciated however, that the preferred route may vary with for example the condition of the recipient.

For each of the above-indicated utilities and indications the amounts required of the active ingredient (as above defined) will depend upon a number of factors including the severity of the condition to be treated and the identity of the recipient and will ultimately be at the discretion of the attendant physician or veterinarian. In general however, for each of these utilities and indications, a suitable effective dose will be in the range of 0.01 to 250 mg per kilogram body weight of recipient per day, advantageously in the range of 0.1 to 100 mg per kilogram body weight per day, preferably in the range of 0.5 to 30 mg per kilogram body weight per day, particularly 1.0 to 30 mg per kilogram body weight per day (unless otherwise indicated, all weights of the active ingredient are calculated with respect to the free base of the compound of formula (I)). The desired dose is preferably presented as one, two, three or four or more sub doses administered at appropriate intervals throughout the day. These sub-doses may be administered in unit dosage forms, for example, containing about 10 to 1200 mg, or 50 to 500 mg, preferably about 20 to 500 mg, and most preferably 100 to 400 mg of active ingredient per unit dose form.

While it is possible for the active ingredient to be administered alone, it is preferable to present it as a pharmaceutical formulation. The formulation comprises the active ingredient as above defined, together with one or more pharmaceutically acceptable excipients therefor and optionally other therapeutic ingredients. The excipient(s) must be "acceptable" in the sense of being compatible with the other ingredients of the formulation and not deleterious to the recipient thereof.

The formulations include those suitable for oral administration and may conveniently be presented in unit dosage form prepared by any of the methods well known in the art of pharmacy. Such methods include the step of bringing into association the active ingredient with the carrier which constitutes one or more accessory ingredients. In general, the formulations are prepared by uniformly and intimately bringing in to association the active ingredient with liquid carriers or finely divided solid carriers or both, and then, if necessary, shaping the product.

Formulations of the present invention suitable for oral administration may be presented as discrete units such as capsules, cachets, sachets of granules or tablets (such as a swallowable, dispersible or chewable tablet) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored any may be formulated so as to provide slow or controlled release of the active ingredient therein.

In addition to the oral dosage forms described hereinabove, the anhydrous crystalline forms and solvates of the present invention may also be formulated for administration by topical, parenteral, and other administration routes using the carriers and techniques described in WO96/01833. It will be appreciated by those skilled in the art that the preparation of dosage forms as solutions of the anhydrous crystalline forms or solvates substantially completely dissolved in a solvent, e.g. for parenteral administration, will preclude the identification of the particular crystalline form utilized in the preparation of the solution. Nevertheless, each of the anhydrous crystalline forms and solvates can be used for the preparation of solutions by substantially completely solubilizing the crystalline form or solvate in a suitable solvent Preferred unit dosage formulations are those containing a daily dose or unit daily sub-dose (as herein above recited) or an appropriate fraction thereof, of the active ingredient.

It should be understood that in addition to the ingredients particularly mentioned above the formulation of this invention may include other agents conventional in the art having regard to the type of formulation in question, for example those suitable for oral administration may include flavoring agents or taste masking agents.

The following examples are intended for illustration only and are not intended to limit the scope of the invention in any way.

EXAMPLE 1

5,6,-Dichloro-2-(isopropylamino)-1-β-L-ribofuranosyl-1H-benzimidazole Form I

The compound of formula (I) (200 mg) was placed in a Thermal Activity Monitor (TAM) and a few drops of water were added to make the powder wet. The vial was sealed and placed in a TAM chamber at 50° C. The mixture was cooled to ambient temperature and filtered. The damp residue was dried in vacuo at 60° C. overnight to give the compound of formula (I) Form I.

Figure 1:
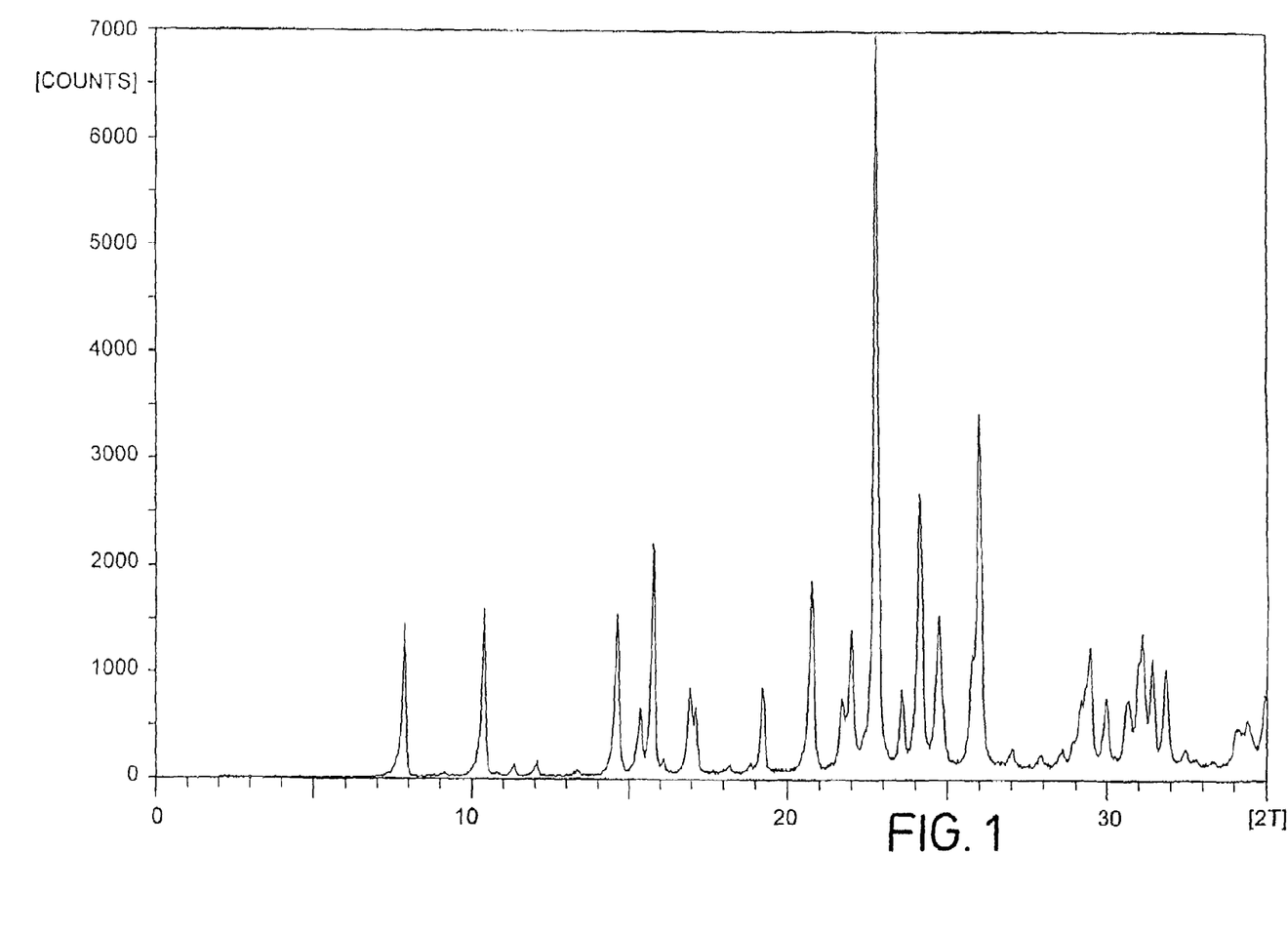
FIG. 1. X-ray powder diffraction pattern of Form I of the compound of formula (I). This pattern was obtained in accordance with the procedures set forth in Example 18.

The X-ray powder diffraction pattern of the product of Example 1 is shown in FIG. 1.

EXAMPLE 2

5,6,-Dichloro-2-(isopropylamino)-1-β-L-ribofuranosyl-1H-benzimidazole Form I

The compound of formula (I) (1.5 g) was suspended in water (30 ml) and heated to 65° C. with stirring. After approximately 0.5 h, stirring became difficult as a gum formed. After further heating, the gum turned solid and was broken up with a spatula. The mixture was heated at 65-70° C. for 9 h. The mixture was cooled to 20° C. and the solid collected by filtration and dried in vacuo at 40° C. for 24 h to give the compound of formula (I) Form I.

The X-ray powder diffraction pattern of the product of Example 2 is shown in FIG. 1.

EXAMPLE 3

5,6,-Dichloro-2-(isopropylamino)-1-β-L-ribofuranosyl-1H-benzimidazole Form I

The compound of formula (I) (5 g) and water (1.5 ml) were stirred and heated in an oil bath at 80° C. The powder turned to a gum and stirring ceased. Heating was continued for 8 h. The solid was loosened with a spatula and stirred occasionally. After cooling to 20° C., the solid was collected and dried in vacuo at 40° C. for 4 h.

The X-ray powder diffraction pattern of the product of Example 3 is shown in FIG. 1.

EXAMPLE 4

5,6,-Dichloro-2-(isopropylamino)-1-β-L-ribofuranosyl-1H-benzimidazole Form I

The compound of formula (I) (2 g) in toluene (15 ml) was heated at reflux for 19 h. On heating the suspension turned to a gum that solidified on further heating. The solid was collected by filtration and dried in vacuo at 40° C. to yield the compound of formula (I).

The X-ray powder diffraction pattern of the product of Example 4 is shown in FIG. 1.

EXAMPLE 5

Preparation of 5,6,-dichloro-2-(isopropylamino)-1-β-L-ribofuranosyl-1H-benzimidazole Form I from Form II The compound of formula (I) Form II (2 g) in toluene (10 ml, 5 vol) was heated to 60° C., at which point the solid began to stick to the sides of the flask. On continued heating to 95° C., an oil formed. Heating was continued to 105° C., then toluene (2.5 vol) was added and heating continued. Reflux was continued for 3 h with rapid stirring. The oil bath temperature was reduced to 80° C. (internal temperature 73° C.) and heating continued for 3 h again with rapid stirring. The mixture was heated to reflux again for 16 h and then allowed to cool to room temperature. The loose solid was collected by filtration washing with toluene (2×5 ml) and dried in vacuo at 20° C. and at 40° C. in vacuo to yield a white solid. The residual solid was removed from the flask, collected by filtration, and dried in vacuo at 20° C. The filtrate was concentrated under reduced pressure to yield a solid.

The X-ray powder diffraction pattern of the product of Example 5 is shown in FIG. 1.

EXAMPLE 6

Preparation of 5,6,-dichloro-2-(isopropylamino)-1-β-L-ribofuranosyl-1H-benzimidazole Form I from Form II The compound of formula (I) (5 g) was stirred with water (1.5 ml) in an oil bath at 80° C. When the temperature of the oil bath reached about 60° C., the mixture became difficult to stir. Heating continued for 8 h with occasional stirring and then cooled to room temperature. The material was dried in vacuo at 40° C. for 4 h The X-ray powder diffraction pattern of the product of Example 6 is shown in FIG. 1.

EXAMPLE 7

5,6,-Dichloro-2-(isopropylamino)-1-β-L-ribofuranosyl-1H-benzimidazole Form II

The compound of formula (I) (100 g) was added to stirred toluene/methanol (4:1, 440 ml) and heated to 65° C. to give a clear solution. The solution was clarified through a filter with a line wash (toluene/methanol [4:1, 110 ml, warm]). The solution was heated back to 65° C. and toluene (4.5 vol) was added slowly, maintaining internal temperature above 65° C. When the addition was complete, the solution was cooled to 40° C. over 1 h and aged at 40° C. After 0.5 h, the mixture was seeded with the compound of formula (I) Form II and then aged for a further 4.5 h. The suspension was cooled to 20° C. over 1 h and aged at 20° C. for 12 h and then cooled to 5° C. over 1 h and aged for 3 h. The solid was collected by filtration, washing with toluene (2×100 ml). The wet cake was transferred to a dryer and dried in vacuo at 20° C.

Figure 2:
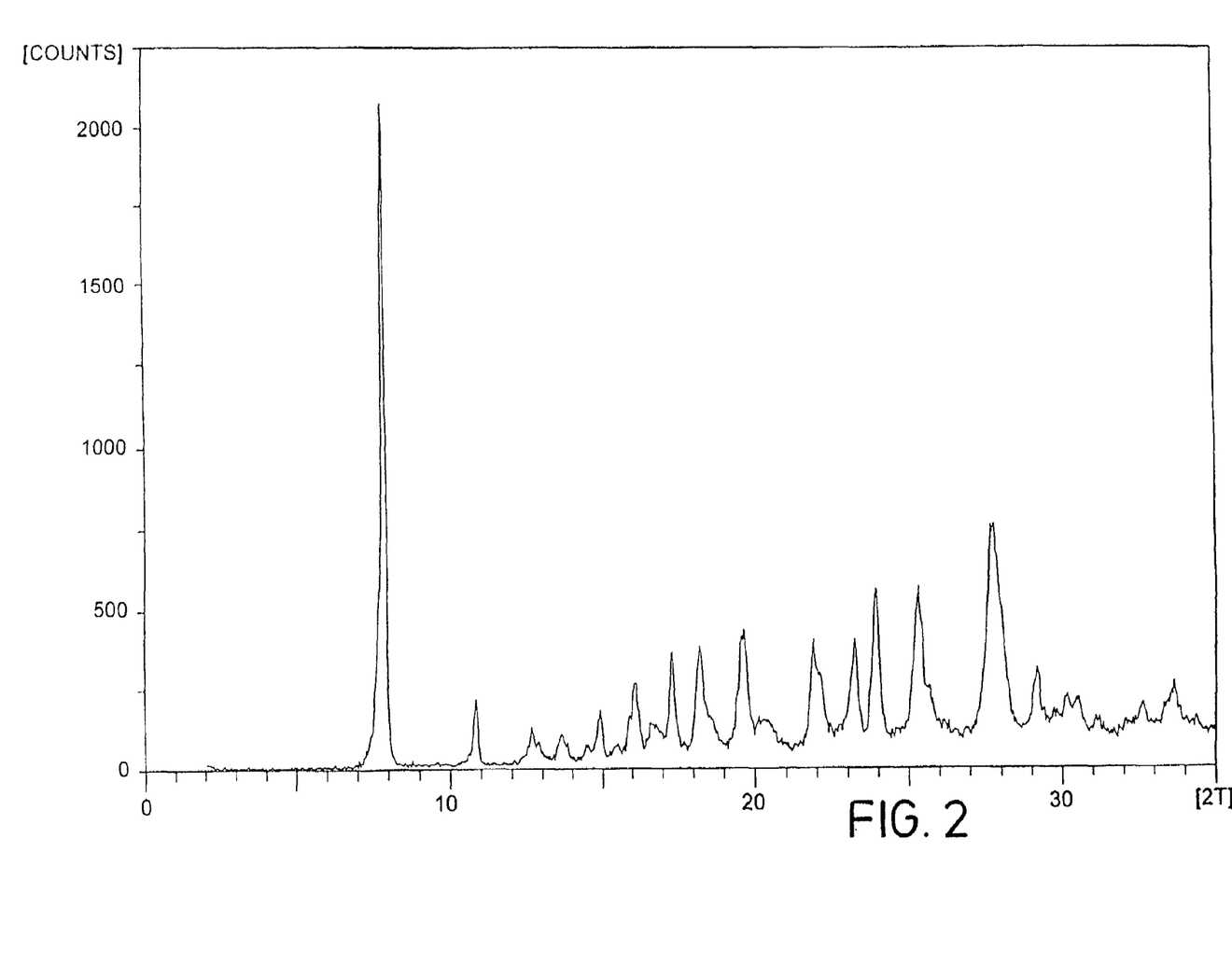
FIG. 2. X-ray powder diffraction pattern of Form II of the compound of formula (I). This pattern was obtained in accordance with the procedures set forth in Example 18.

The X-ray powder diffraction pattern of the product of Example 7 is shown in FIG. 2.

EXAMPLE 8

5,6,-Dichloro-2-(isopropylamino)-1-β-L-ribofuranosyl-1H-benzimidazole Form II

The compound of formula (I) (1.0 wt) was dissolved in ethyl acetate (6.0 vol) and subjected to a finishing filtration. The filtrates were concentrated to approximately 3 volumes. Assuming complete solvent exchange, the solution was reconstituted to 3.5 volumes with methanol. Water (0.5 vol) was added and the solution was cooled to 0-5° C. The crystallization was seeded with a small amount of pure the compound of formula (I) and the solution was stored at 0-5°

C. for 2 h. The product was filtered (no wash) and dried in vacuo for 24-48 h at ambient temperature. A second crop was obtained by evaporation of the filtrate to half volume followed by cooling, seeding, and crystallization in a similar manner as above.

The X-ray powder diffraction pattern of the product of Example 8 is shown in FIG. 2.

EXAMPLE 9

5,6,-Dichloro-2-(isopropylamino)-1-β-L-ribofuranosyl-1H-benzimidazole Form II

The compound of formula (I) (10 g) was dissolved in methanol (20 ml) with heating to 50° C. Water (5 ml) was added and the mixture cooled to 5° C. slowly and was stirred at 5° C. for 1 h. The solid was collected by filtration and dried in vacuo at 20° C. for 15 h and at 40° C. for 4 h to yield the compound of formula (I).

The X-ray powder diffraction pattern of the product of Example 9 is shown in FIG. 2.

EXAMPLE 10

Preparation of mixtures of 5,6,-dichloro-2-(isopropylamino)-1-β-L-ribofuranosyl-1H-benzimidazole forms The compound of formula (I) may be dissolved in 2N hydrochloric acid (60 ml) and stirred for 0.5 h and filtered. The filtrate was heated to 60° C. and 2N sodium hydroxide (55 ml) was added slowly, maintaining the internal temperature between 60-70° C. during the addition. The mixture was stirred at 65-70° C. for 2 h and then cooled to 20° C. over 2 h. The solid was collected by filtration, washing with water (2×30 ml) and dried in vacuo at 40° C. for 16 h to yield the compound of formula (I) (8.8 g, 88%).

EXAMPLE 11

5,6,-Dichloro-2-(isopropylamino)-1-β-L-ribofuranosyl-1H-benzimidazole ethanolate The compound of formula (I) (1.0 wt) was suspended in ethanol/water (10.0 vol) at 70° C. for 2 h. The ethanol/water (v/v) ratios were as follows: 10/90, 15/85, 20/80, 25/75 and 30/70. The resulting solid white free flowing powder was filtered and air-dried. Ethanol solvate was obtained in similar manner from solutions of ethanol/toluene (ratios 5/95, 10/90, 15/85, 20/80, 25/75, and 30/70).

Figure 3:
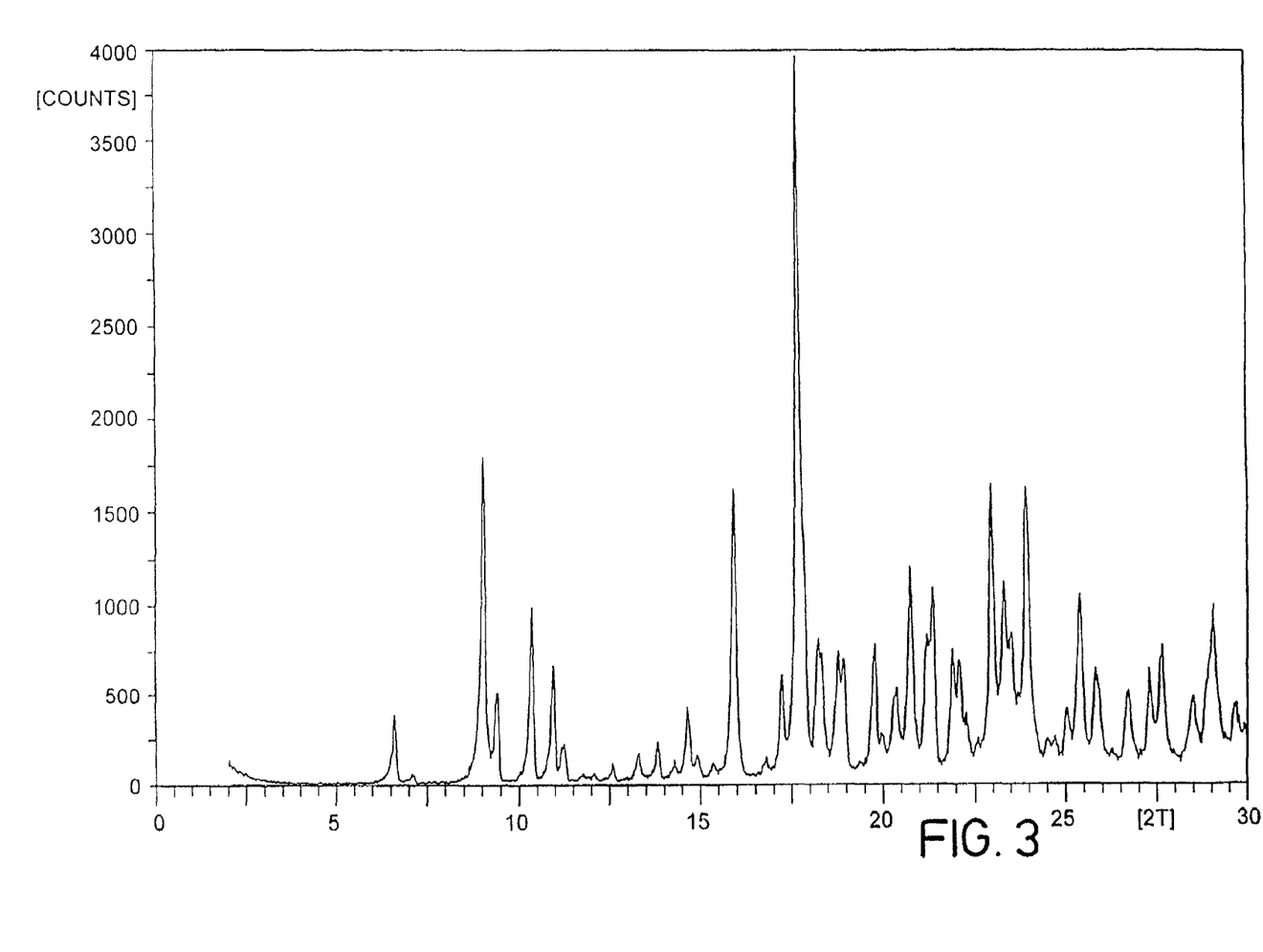
FIG. 3. X-ray powder diffraction pattern of the ethanolate of the compound of formula (I). This pattern was obtained in accordance with the procedures set forth in Example 18.

The X-ray powder diffraction pattern of the product of Example 11 is shown in FIG. 3.

EXAMPLE 12

5,6,-Dichloro-2-(isopropylamino)-1-β-L-ribofuranosyl-1H-benzimidazole ethanolate The compound of formula (I) (20 g) was added to stirred toluene/ethanol (7:1, 200 ml) and heated to reflux (81° C.) to give a clear solution. The solution was cooled to 20° C. and crystallization occurred at approximately 50° C. The suspension was cooled to 0-5° C. and aged for 2 h. The solid was collected by filtration, and washed with toluene (2×20 ml). The wet cake was dried in vacuo at 40° C.

Recrysallization of the compound of formula (I) from ethanol/water or ethanol/toluene gave an ethanol solvate containing 0.5 moles of ethanol per mole of the compound of formula (I).

The X-ray powder diffraction pattern of the product of Example 12 is shown in FIG. 3.

EXAMPLE 13

5,6,-Dichloro-2-(isopropylamino)-1-β-L-ribofuranosyl-1H-benzimidazole Form IV

Water (300 ml) was added to Form I (4 g) as prepared in Example 1 above and stirred for 20 min. The mixture was then heated at 50° C. for 6 days, and then cooled to room temperature. The solid, grainy crystalline material was filtered and dried in vacuo at 60° C.

Figure 4:
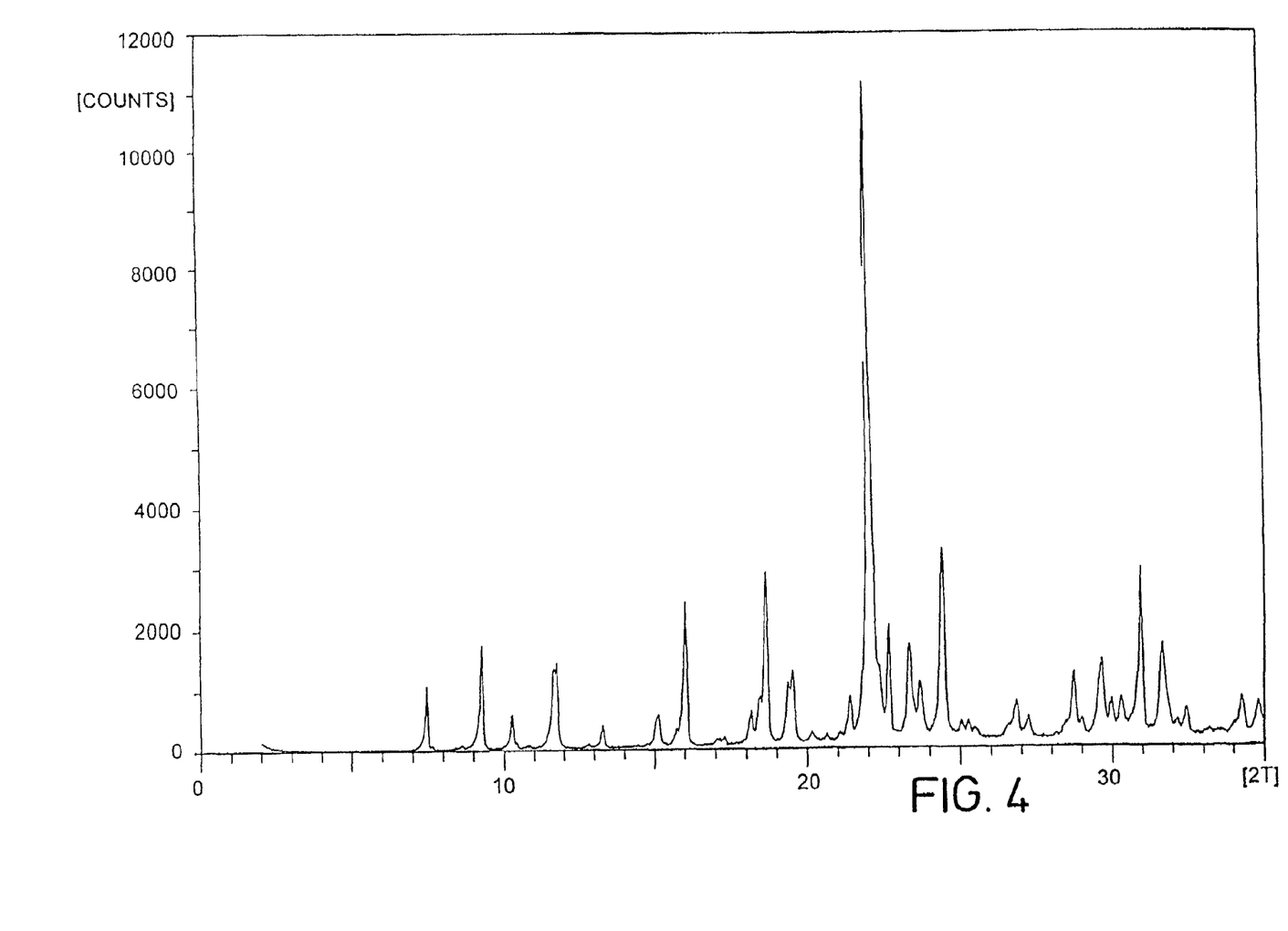
FIG. 4. X-ray powder diffraction pattern of Form IV of the compound of formula (I). This pattern was obtained in accordance with the procedures set forth in Example 18.

The X-ray powder diffraction pattern of the product of Example 13 is shown in FIG. 4.

EXAMPLE 14

5,6,-Dichloro-2-(isopropylamino)-1-β-L-ribofuranosyl-1H-benzimidazole Form V

The compound of formula (I) (2.0 g) was added gradually to water (40 ml) at 70° C. with rapid stirring over 2 h. after heating at 65-70° C. with stirring for an additional 7 h, the heating and stirring were discontinued. After sitting for 2.5 days at ambient temperature, the mixture was filtered the grainy white solid residue was allowed to air dry overnight affording the compound of formula (I) Form V.

Figure 5:
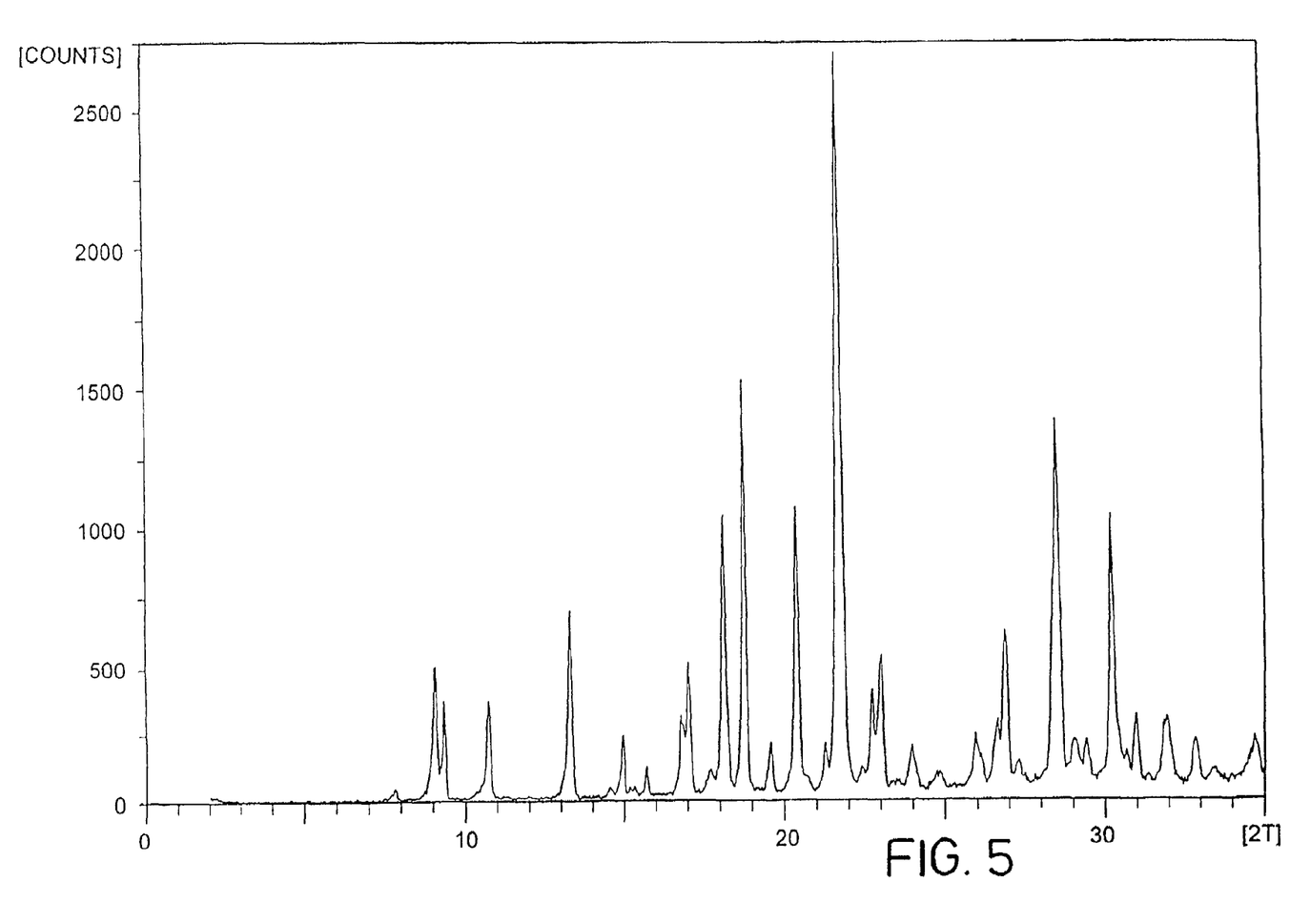
FIG. 5. X-ray powder diffraction pattern of Form V of the compound of formula (I). This pattern was obtained in accordance with the procedures set forth in Example 18.

The X-ray powder diffraction pattern of the product of Example 14 is shown in FIG. 5.

EXAMPLE 15

5,6,-Dichloro-2-(isopropylamino)-1-β-L-ribofuranosyl-1H-benzimidazole Form V

The compound of formula (I) Form VI (72.86 mg), was added to 1 ml of acetonitrile and completely dissolved. Upon standing for about 30 days at ambient temperature, large crystals precipitated out of the solution, affording the compound of formula (I) Form V.

The X-ray powder diffraction pattern of the product of Example 15 is shown in FIG. 5.

EXAMPLE 16

5,6,-Dichloro-2-(isopropylamino)-1-β-L-ribofuranosyl-1H-benzimidazole Form VI

The compound of formula (I) ethanolate (200 mg) was weighed into small vials. Hydrostats with NaCl saturated solutions and excess NaCl solid were inserted inside the vials. The vials were then sealed very well and stored at 80° C. The samples were removed from the vial and heated to 170° C. on a differential scanning calorimeter and subsequently cooled to room temperature. The powder was collected from DSC pans and analyzed by X-ray diffraction.

Figure 6:
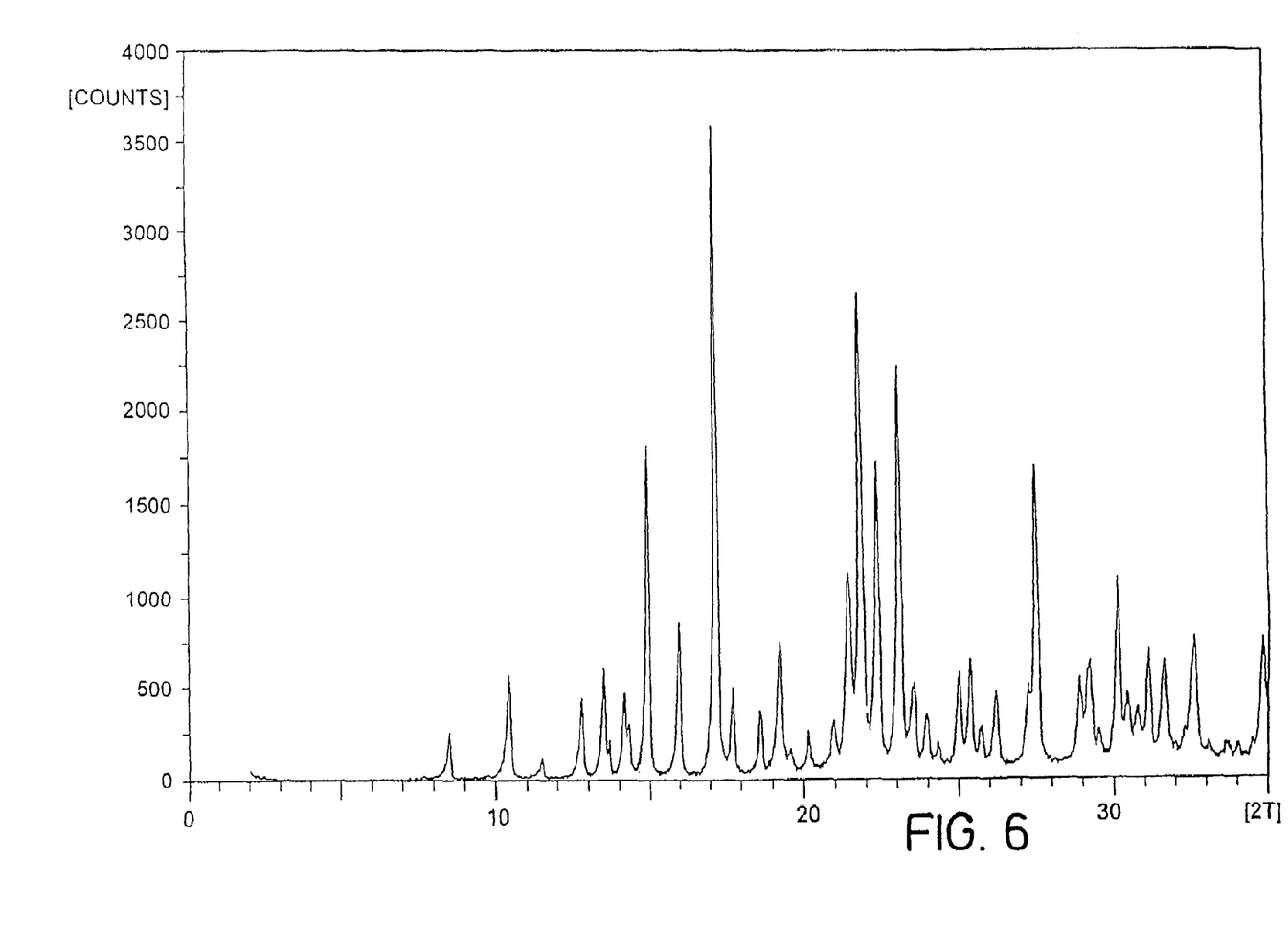
FIG. 6. X-ray powder diffraction pattern of Form VI of the compound of formula (I). This pattern was obtained in accordance with the procedures set forth in Example 18.

Characterization: The X-ray powder diffraction pattern of the product of Example 16 (Form VI) is shown in FIG. 6. The following data, measured in 2 theta angles, d-spacings, relative intensities, and Miller indices were obtained:

TABLE 1

X-ray Powder Diffraction of Form VI of 1263W94

| 2 θ(°)[1] | Å[2] | I | h[3] | k[3] | l[3] |
|---|---|---|---|---|---|
| 8.53 | 10.36 | 14.5 | 0 | 0 | 4 |
| 10.47 | 8.45 | 25.6 | 1 | 0 | 2 |
| 12.80 | 6.91 | 16.8 | 0 | 0 | 6 |
| 14.16 | 6.25 | 16.4 | 1 | 1 | 2 |
| 13.51 | 6.55 | 21.4 | 1 | 1 | 0 |
| 14.95 | 5.92 | 60.4 | 1 | 1 | 3 |
| 15.98 | 5.54 | 26.2 | 1 | 1 | 4 |
| 17.23 | 5.14 | 100.0 | 1 | 1 | 5 |
| 19.25 | 4.61 | 19.3 | 2 | 0 | 1 |
| 21.41 | 4.15 | 26.5 | 2 | 1 | 0 |
| 21.83 | 4.07 | 60.4 | 2 | 1 | 2 |
| 22.35 | 3.97 | 38.3 | 2 | 1 | 3 |
| 23.07 | 3.85 | 48.7 | 2 | 1 | 4 |
| 27.49 | 3.24 | 30.9 | 2 | 1 | 8 |
| 30.11 | 2.97 | 18.5 | 2 | 2 | 6 |

[1]Margin of error is approx. ±0.05 degrees.
[2]Margin of error is approx. ±0.05 Å.
[3]The Miller indices, h, k, and l above are used to define uniquely a set of parallel planes in the crystal.

EXAMPLE 17

Preparation of 5,6-dichloro-2-(isopropylamino)-1-(beta-L-ribofuranosyl)-1H-benzimidazole Form VI by Crystallization from Ethyl Acetate/Toluene Sodium hydroxide (2M, 1790 ml) was added to a slurry of 5,6-dichloro-2-(isopropylamino)-1-(2,3,5-tri-O-acetyl-beta-L-ribofuranosyl)-1H-benzimidazole(358 g) in TMBE (1790 ml) containing methanol (179 ml). The mixture was stirred at 25-30° C. until the reaction was complete. The layers were separated and the aqueous layer further extracted with TBME (716 ml) The combined organic solutions were washed with 10% brine (2×1790 ml). The organic solution was concentrated at atmospheric pressure to about 2.5 vol (895 ml). Ethyl acetate (2864 ml) was added and the solution was again concentrated to about 2.5 vol. The solution was cooled to 40-50° C., and the resulting solution was clarified, rinsing with an ethyl acetate (716 ml) line wash. The clarified solution was concentrated at atmospheric pressure to about 3.3 vol (1180 ml).

The solution was heated to 60° C. Toluene (3000 ml) was heated to 60° C. and added over 1 h to the ethyl acetate solution. The resulting mixture was aged at 60° C. overnight before cooling to 0-5° C. over 1 h then aging at 0.5° C. for about 2 h. The slurry was filtered, washed with ethyl acetate:toluene 1:4 (2×716 ml) and dried in vacuo at 40° C. for 18 h to yield 5,6-dichloro-2-(isopropylamino)-1-(beta-L-ribofuranosyl)-1H-benzimidazole Form VI Characterization: as for Example 16.

EXAMPLE 18

Experimental Methods for Characterization of Crystalline Forms and Solvates

X-Ray Powder Diffraction

The X-ray powder diffraction patterns were determined on a Philips X'Pert MPD diffractometer equipped with diffracted beam curved graphite monochromator using copper Kα X-radiation and an automatic divergent slit. The diffractometer was run in the step scan mode at 0.04° per step and a 1 second count per step. A xenon proportional counter with a graphite monochromator was used as the detector. Samples were back filled into a 16 mm diameter holder having a thickness of about 2 mm. The X-ray Powder Diffraction Patterns of Forms I, II, IV, V, VI and the ethanolate are provided in FIGS. 1, 2, 4, 5, 6 and 3, respectively.

EXAMPLE 19

Tablet Formulation

Formulation A

| | 1263W94 Ethanolate Tablets Direct Compression | |
|---|---|---|
| Potency | 100 mg | 400 mg |
| Core Ingredients | | |
| 1263W94 Ethanolate | 105.9[2] | 423.6[3] |
| Microcrystalline Cellulose, NF | 200.0 | 800.0 |
| Crospovidone, NF | 20.0 | 80.0 |
| Magnesium Stearate, NF | 0.8 | 3.2 |
| Total (core) | 326.7 mg | 1306.8 mg |
| Coating Ingredients | | |
| Opadry White YS-1-18034 | 9.0 | 36.0 |
| Purified Water USP[1] | QS | QS |
| Total (core) | 335.7 mg | 1342.8 mg |
| Theoretical Batch Size (cores) | | |
| kg | 0.8168 | |
| tablets | 2500 | |

[1]Removed during processing
[2]Equivalent to 100 mg of 1263W94 per tablet
[3]Equivalent to 400 mg of 1263W94 per tablet

| | 1263W94 Tablets (form II/amorphous) Direct Compression | |
|---|---|---|
| Potency | 100 mg | 400 mg |
| Core Ingredients | | |
| 1263W94 | 103.3[2] | 413.2[3] |
| Lactose, anhydrous, NF | 65.0 | 260.0 |
| Microcrystalline Cellulose, NF | 20.0 | 80.0 |
| Crospovidone, NF | 12.0 | 48.0 |
| Magnesium Stearate, NF | 1.0 | 4.0 |
| Total (core) | 201.3 mg | 805.2 mg |
| Coating ingredients | | |
| Opadry White YS-1-18034 | 6.0 | 24.0 |
| Purified Water USP[1] | QS | QS |
| Total (core) | 207.3 mg | 829.2 mg |
| Theoretical Batch Size (cores) | | |
| kg | 0.785 | |
| tablets | 3900 | |

[1]Removed during processing
[2]Equivalent to 100 mg of 1263W94 per tablet
[3]Equivalent to 400 mg of 1263W94 per tablet Manufacturing Procedure for Direct Compression All ingredients were screened, except the magnesium stearate, using 20 or 30 mesh. All ingredients were blended, excluding the magnesium stearate, until uniform. The magnesium stearate was screened as above. The magnesium stearate was added to the other ingredients and blended. The tablets were compressed using a rotary press. A 10% coating suspension was prepared by mixing Opadry with water. Tablets were coated to a weight gain of approximately 3%.

Formulation B

| 1263W94 Ethanolate Tablets Wet Granulation | | |
|---|---|---|
| Potency | 100 mg | 400 mg |
| Core Ingredients | | |
| 1263W94 Ethanolate | 105.9[2] | 423.6[3] |
| Microcrystalline Cellulose, NF | 75.0 | 300.0 |
| Crospovidone, NF | 15.0 | 60.0 |
| Povidone, USP, K30 | 7.5 | 30.0 |
| Magnesium Stearate, NF | 0.6 | 2.4 |
| Purified Water USP[1] | QS | QS |
| Total (core) | 204.0 mg | 816.0 mg |
| Coating Ingredients | | |
| Opadry White YS-1-18034 | 6.0 | 24.0 |
| Purified Water USP[1] | QS | QS |
| Total (core) | 210.0 mg | 840.0 mg |
| Theoretical Batch Size (cores) | | |
| kg | 0.714 | |
| tablets | 3500 | |

[1]Removed during processing
[2]Equivalent to 100 mg of 1263W94 per tablet
[3]Equivalent to 400 mg of 1263W94 per tablet

| 1263W94 Tablets (form II/amorphous) Wet Granulation | | |
|---|---|---|
| Potency | 100 mg | 400 mg |
| Core Ingredients | | |
| 1263W94 | 103.3[2] | 413.2[3] |
| Lactose, anhydrous, NF | 60.0 | 240.0 |
| Microcrystalline Cellulose, NF | 20.0 | 80.0 |
| Crospovidone, NF | 12.0 | 48.0 |
| Povidone, USP, K30 | 6.0 | 24.0 |
| Sodium Lauryl Sulfate, NF | 2.0 | 8.0 |
| Colloidal Silicon Dioxide, NF | 0.6 | 2.4 |
| Magnesium Stearate, NF | 1.0 | 4.0 |
| Purified Water USP[1] | QS | QS |
| Total (core) | 204.9 mg | 819.6 mg |
| Coating Ingredients | | |
| Opadry White YS-1-18034 | 6.0 | 24.0 |
| Purified Water USP[1] | QS | QS |
| Total (core) | 210.9 mg | 843.6 mg |
| *—continued* | | |
| 1263W94 Tablets (form II/amorphous) Wet Granulation | | |
| Potency | 100 mg | 400 mg |
| Theoretical Batch Size (cores) | | |
| kg | 0.799 | |
| tablets | 3900 | |

[1]Removed during processing
[2]Equivalent to 100 mg of 1263W94 per tablet
[3]Equivalent to 400 mg of 1263W94 per tablet Manufacturing Procedure for Wet Granulation The granule ingredients were screened using a 20 or 30 mesh. The granule ingredients were dry blended in a high shear granulator until uniform and then granulated in a high shear granulator using purified water. The granule was dried to a loss on drying of less than 2%. The granule was screened as above. The remaining ingredients were screened as above. The granule was blended with the remaining ingredients. The tablets were compressed using a rotary press. A 10% coating suspension was prepared by mixing Opadry with water. Tablets were coated to a weight gain of approximately 3%.

EXAMPLE 20

Capsule Formulation

The following formulation may be prepared as follows using the compound of formula (I) Form II.

| 1263W94 Capsules (form II) | |
|---|---|
| Potency | 100 mg |
| Capsule Fill Ingredients | |
| 1263W94 (active) | 101.0[1] |
| Lactose, Anhydrous NF | 232.0 |
| Crospovidone, NF | 17.0 |
| Magnesium Stearate, NF | 1.0 |
| Total Fill Weight | 351.0 mg |
| Capsule Shell | |
| Gelatin, while opaque cap and body | 81.1 |
| Total Weight | 432.5 mg |

[1]Equivalent to 100 mg of 1263W94 per tablet

Manufacturing Procedure for Capsules

The capsule fill ingredients are mixed using a mortar and pestle by geometric dilution. The combined capsule fill ingredients are filled into the gelatin capsules by hand. Capsules are closed by hand.

EXAMPLE 21

Oral Suspension Formulation

The following formulation may be prepared as follows using the compound of formula (I) Form I, II, V or an admixture of Forms I and V.

| 1263W94 Oral Suspension | |
|---|---|
| Potency | 30 mg/ml |
| Ingredients | per 100 ml |
| 1263W94 (active) | 3.0 g |
| Sucrose | 50.0 g |
| Propylene Glycol | 5.0 g |
| Sodium Chloride | 0.5 g |
| Citric Acid | QS |
| Sodium Citrate | QS |
| Microcrystalline Cellulose and Sodium Carboxymethylcellulose | 2.5 g |
| Sodium Carboxymethylcellulose | 0.25 g |
| Polysorbate 80 | 0.2 g |
| Sodium Benzoate | 0.1 g |
| Methylparaben | 0.1 g |
| Flavorant | 0.2 ml |
| Colorant | 0.005 g |
| Purified Water USP | QS |
| Total Volume | 100.0 ml |

Manufacturing Procedure for Oral Solution

Sucrose is dissolved in purified water to approximately 70% of total batch volume. While mixing continuously, sodium chloride, citric acid, sodium citrate, and sodium benzoate are added and dissovled. If necessary, the pH is adjusted to between 5.0 and 6.0, by adding sufficient citric acid or sodium citrate as necessary. Microcrystalline cellulose and sodium carboxymethylcellulose (Avicel RC 591) are added while mixing and mixing is continued until a uniform, smooth dispersion is formed. Polysorbate 80 is added while mixing. In a separate vessel, methylparaben is dissolved in propylene glycol and sodium carboxy methyl cellulose (0.25 g) is dispersed, and this liquid is added to the bulk dispersion while mixing. The active ingredient is gradually dispersed in the bulk liquid while mixing continuously, to produce a uniform dispersion. Flavorant and Colorant are added and the volume is adjusted to 100 ml by addition of purified water. The suspension is then homogenized by passing through a pump and a colloid mill.

The foregoing Examples are illustrative of the present invention and are not to be construed as limiting thereof. The invention is defined by the following claims including equivalents thereof.

The invention claimed is:

1. A pharmaceutical composition comprising a crystalline form of Form II 5,6-dichloro-2-(isopropylamino)-1-β-L-ribofuranosyl-1H-benzimidazole having substantially the same X-ray powder diffraction pattern as FIG. 2, wherein said X-ray powder diffraction pattern is obtained with a diffractometer equipped with a diffracted beam curved graphite monochromator using copper Kα X-radiation, and at least one pharmaceutically acceptable carrier therefor.

2. A method for the treatment of a herpes viral infection in a human which comprises administering to the human host, an effective antiviral amount of a crystalline form of Form II 5,6-dichloro-2-(isopropylamino)-1-β-L-ribofuranosyl-1H-benzimidazole having substantially the same X-ray powder diffraction pattern as FIG. 2, wherein said X-ray powder diffraction pattern is obtained with a diffractometer equipped with a diffracted beam curved graphite monochromator using copper Kα X-radiation.

3. A pharmaceutical composition comprising a crystalline form of 5,6-dichloro-2-(isopropylamino)-1-β-L-ribofuranosyl-1H-benzimidazole having substantially the same X-ray powder diffraction pattern as FIG. 3, wherein said X-ray powder diffraction pattern is obtained with a diffractometer equipped with a diffracted beam curved graphite monochromator using copper Kα X-radiation, and at least one pharmaceutically acceptable carrier therefor.

4. A pharmaceutical composition comprising a crystalline form of Form V 5,6-dichloro-2-(isopropylamino)-1-β-L-ribofuranosyl-1H-benzimidazole having substantially the same X-ray powder diffraction pattern as FIG. 5, wherein said X-ray powder diffraction pattern is obtained with a diffractometer equipped with a diffracted beam curved graphite monochromator using copper Kα X-radiation, and at least one pharmaceutically acceptable carrier therefor.

5. A pharmaceutical composition comprising an admixture of two or more forms or solvates of 5,6-dichloro-2-(isopropylamino)-1-β-L-ribofuranosyl-1H-benzimidazole selected from the group consisting of Form I, Form II, ethanol solvate, Form IV, Form V, and amorphous, and at least one pharmaceutically acceptable carrier therefor.

6. A method for the treatment of a herpes viral infection in a human which comprises administering to the human host, an effective antiviral amount of a crystalline form of 5,6-dichloro-2-(isopropylamino)-1-β-L-ribofuranosyl-1H-benzimidazole having substantially the same X-ray powder diffraction pattern as FIG. 3, wherein said X-ray powder diffraction pattern is obtained with a diffractometer equipped with a diffracted beam curved graphite monochromator using copper Kα X-radiation.

7. A method for the treatment of a herpes viral infection in a human which comprises administering to the human host, an effective antiviral amount of a crystalline form of Form V 5,6-dichloro-2-(isopropylamino)-1-β-L-ribofuranosyl-1H-benzimidazole having substantially the same X-ray powder diffraction pattern as FIG. 5, wherein said X-ray powder diffraction pattern is obtained with a diffractometer equipped with a diffracted beam curved graphite monochromator using copper Kα X-radiation.

8. A method for the treatment of a herpes viral infection in a human which comprises administering to the human host, an effective antiviral amount of a composition comprising an admixture of two or more crystalline forms or solvates of 5,6-dichloro-2-(isopropylamino)-1-β-L-ribofuranosyl-1H-benzimidazole selected from the group consisting of Form I, Form II, ethanol solvate, Form IV, Form V, and amorphous.

* * * * *